United States Patent
Axelsson et al.

(10) Patent No.: US 8,158,822 B2
(45) Date of Patent: Apr. 17, 2012

(54) PROCESS FOR PRODUCING POTASSIUM FORMATE

(75) Inventors: Goran Axelsson, Hoor (SE); Christoffer Paulsson, Eslov (SE); Par Fredholm, Helsingborg (SE)

(73) Assignee: Perstorp Specialty Chemicals AB, Perstorp (SE)

(*) Notice: Subject to any disclaimer, the term of this patent is extended or adjusted under 35 U.S.C. 154(b) by 310 days.

(21) Appl. No.: 12/521,807

(22) PCT Filed: Nov. 30, 2007

(86) PCT No.: PCT/SE2007/001060
§ 371 (c)(1),
(2), (4) Date: Jun. 30, 2009

(87) PCT Pub. No.: WO2008/091186
PCT Pub. Date: Jul. 31, 2008

(65) Prior Publication Data
US 2010/0087678 A1    Apr. 8, 2010

(30) Foreign Application Priority Data
Jan. 24, 2007    (SE) .................................... 0700161

(51) Int. Cl.
*C07C 53/00*    (2006.01)
(52) U.S. Cl. ...................................... 562/609

(58) Field of Classification Search .................. None
See application file for complete search history.

(56) References Cited

U.S. PATENT DOCUMENTS 2,281,715 A * 5/1942 Atwater .................. 562/609

FOREIGN PATENT DOCUMENTS

| CN | 1443746 | 9/2003 |
| WO | 96/01249 | 1/1996 |

* cited by examiner

*Primary Examiner* — Paul A Zucker
(74) *Attorney, Agent, or Firm* — Oblon, Spivak, McClelland, Maier & Neustadt, L.L.P.

(57) ABSTRACT

The present invention relates to a process for producing potassium formate. Formaldehyde, potassium hydroxide and isobutyraldehyde are reacted in water, at a molar ratio of 1.0:1.0:1.0 to 3.0:2.0:1.0 and at a temperature of 0-1000 C, preferably 30-700 C. The obtained reaction solution is neutralised to pH 4-6 and evaporated in a first step, whereby two phases are obtained, one organic phase and one aqueous phase, the latter comprising the main part of the potassium formate. The organic phase is subsequently separated from the aqueous phase, where after a final evaporation of the aqueous phase takes place at a pressure of 0.0-1.0 bar and a temperature of 160-2500 C, to obtain a melt of potassium formate. Water is added followed by filtration resulting in a solution having a content of >99% by weight of potassium formate, calculated on a water free basis.

13 Claims, No Drawings

PROCESS FOR PRODUCING POTASSIUM FORMATE

The present invention refers to a process for producing potassium formate.

A process for producing potassium formate is described in detail in the European patent, EP0769000B1 and to avoid replication regarding the process description references are made to this document. Different application areas for potassium formate are also described in said patent. Industrially potassium formate is usually produced according to the reaction formula below:

$$2\,HCHO + KOH + CH_3CH(CH_3)CHO \longrightarrow HCOOK + HOCH_2C(CH_3)_2CH_2OH$$

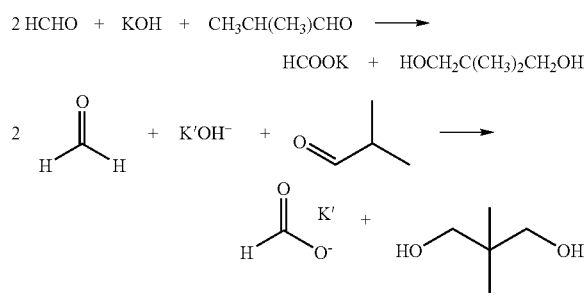

The process described in EP0769000B1 works perfectly well but the purification process of potassium formate is just generally described. There is a great need for producing potassium formate in pure form and how this could be done is not known in the prior art.

According to the present invention the above described need is met and a process for producing potassium formate is accomplished, whereby formaldehyde, potassium hydroxide and isobutyraldehyde are reacted in water, at a molar ratio of 1.0:1.0:1.0 to 3.0:2.0:1.0, such as 1.5:1.2:1.0 to 2.5:1.2:1.0 to 2.5:1.7:1.0 or 1.8:1.0:1.0 to 2.2:1.5:1.0 and at a temperature of 0-100° C., preferably 30-70° C. The process is characterised in that the reaction solution obtained is neutralised to pH 4-6 and evaporated, whereby two phases are obtained, one aqueous phase, containing the main part of the potassium formate and one organic phase. The organic phase is subsequently separated from the aqueous phase, where after a final evaporation of the aqueous phase takes place at a pressure of 0.0-1.0 bar, preferably 0.0-0.5 bar or rather 0.0-0.2 bar and a temperature of 160-250° C., to obtain a melt of potassium formate. Water is added to the melt, whereby an aqueous solution is obtained, which solution is filtrated, for example through a coal filter. The result is a solution having a content of >99% by weight of potassium formate, calculated on a water free basis.

The final evaporation of potassium formate may be carried out by one or more evaporators. The pressure at the final evaporation is preferably 0.0-0.2 bar and the temperature is preferably 160-200° C. The evaporation in the first step is usually carried out until the water content of the solution is 10-40% by weight, preferably 25-35%.

The present invention is further explained with reference to the embodiment examples below, where example 1 refers to a comparison test outside the scope of the invention and example 2 refers to the invention. The examples are to be construed as illustrative and not limiting in any way.

EXAMPLE 1

9058 parts by weight of an aqueous solution having a formaldehyde content of 584 parts by weight were charged in a reactor equipped with a stirrer and a cooler. The temperature of the solution was set to 25° C., where after 1168 parts by weight of a solution having a potassium hydroxide content of 46% by weight were added to the formaldehyde solution during 5 minutes, followed by an addition during 26 minutes of 645 parts by weight of a solution having a isobutyraldehyde content of 98.7% by weight. The added amounts resulted in a mixture where formaldehyde:potassium hydroxide:isobutyraldehyde are present in a molar ratio of 2.2:1.09:1.0. The temperature in the reactor was controlled by the cooler to get a final temperature of 54° C. At this temperature the reaction was allowed to proceed for another 20 minutes. Then the solution was neutralised to a pH of about 5.5 by the addition of 35 parts by weight of a solution having a formic acid content of 85% by weight.

The reaction solution was then evaporated until an increase of the boiling point with 30° C. was reached. The solution was subsequently cooled to 90° C. and allowed to separate during two hours into one aqueous phase and one organic phase. The aqueous phase had a content of 97.5% by weight of potassium formate, 1.5% by weight of neopentyl glycol and 1.0% by weight of other organic compounds, calculated on a water free basis.

EXAMPLE 2

The aqueous phase disclosed at the end of example 1 was heated to 180° C., whereupon the pressure was reduced to 0.1 bar. The solution obtained was then evaporated during 1 hour, generating a melt of potassium formate. Water was added to the melt to obtain a solution of potassium formate with 25% by weight of water. Finally the solution was filtrated through a coal filter, resulting in a solution having a content of 99.6% by weight potassium formate, 0.02% by weight neopentyl glycol and the rest of the solution contained other organic compounds, calculated on a water free basis.

The invention claimed is:

1. A process for producing potassium formate having a purity of more than 99% comprising:
   reacting formaldehyde, potassium hydroxide, and isobutyraldehyde
   at a molar ratio between 1.0:1.0:1.0 and 3.0:2.0:1.0 and at a temperature ranging from 0 to 100° C. to form a reaction solution;
   neutralizing the reaction solution to a pH ranging from 4 to 6 and evaporating it to yield a solution having a water phase and an organic phase;
   evaporating the water phase at a pressure ranging from 0 to 1 bar and at a temperature ranging from 160 to 250° C. to yield a melt of potassium formate;
   adding water to said melt and filtering through a coal filter to provide a potassium formate solution containing potassium formate having a purity of more than 99% calculated on a water-free basis.

2. The process according to claim 1, wherein evaporating the water phase at a pressure ranging from 0 to 1 bar at a temperature ranging from 160 to 250° C. is carried out by one or more evaporators.

3. The process according to claim 1, wherein evaporating the water phase is carried out at a pressure of 0.0-0.2 bar and at a temperature of 160-200° C.

4. The process according to claim 1, wherein the reaction solution is neutralized to a pH 4-6 and evaporated until the water content of the solution is 10-40% by weight.

5. The process according to claim 1, wherein the reaction solution is neutralized to a pH 4-6 and evaporated until the water content of the solution is 25-35%.

6. The process according to claim 1, wherein the molar ratio ranges from 1.5:1.2:1.0 to 2.5:1.2:1.0.

7. The process according to claim 1, wherein formaldehyde, potassium hydroxide and isobutyraldehyde are reacted in water at a temperature of 30-70° C.

8. The process according to claim 1, wherein evaporation of the water phase takes place at a pressure of 0.0-0.5 bar.

9. The process according to claim 1, wherein evaporation of the water phase takes place at a pressure of 0.0-0.2 bar.

10. The process of claim 1, wherein the molar ratio ranges from 1.5:1.2:1.0 and 2.5:1.7:1.0.

11. The process of claim 1, wherein the molar ratio ranges from 1.8:1.0:1.0 and 2.2:1.5:1.0.

12. A process for producing of potassium formate comprising:

reacting formaldehyde, potassium hydroxide, and isobutyraldehyde at a molar ratio between 1.0:1.0:1.0 and 3.0:2.0:1.0 and at a temperature ranging from 0 to 100° C. to form a reaction solution;

neutralizing the reaction solution to a pH ranging from 4 to 6;

evaporating water from the neutralized reaction solution to form a solution having a aqueous phase and an organic phase;

removing the organic phase;

removing water from the aqueous phase at a pressure ranging from 0 to 1 bar and at a temperature ranging from 160 to 250° C. to yield a melt of potassium formate;

adding water to said melt to form an aqueous solution, and filtering the aqueous solution through a coal filter to yield a potassium formate solution containing potassium formate.

13. The method of claim 12 that produces a potassium formate solution that is more than 99% by weight potassium formate calculated on a water-free basis.

* * * * *

UNITED STATES PATENT AND TRADEMARK OFFICE
CERTIFICATE OF CORRECTION

PATENT NO. : 8,158,822 B2  Page 1 of 1
APPLICATION NO. : 12/521807
DATED : April 17, 2012
INVENTOR(S) : Goran Axelsson et al.

It is certified that error appears in the above-identified patent and that said Letters Patent is hereby corrected as shown below:

Title Page, Item (57)
Abstract, line 4 "0-1000 C" should read -- 0-100°C --.
Abstract, line 5 "30-700 C" should read -- 30-70°C --.
Abstract, line 12 "160-2500 C" should read -- 160-250°C --.

Column 1, line 38 "0-100°C.," should read -- 0-100°C, --.
Column 1, line 46 "160-250°C.," should read -- 160-250°C, --.
Column 2, line 2 "25°C.," should read -- 25°C, --.
Column 2, line 17 "30°C." should read -- 30°C --.
Column 2, line 18 "90°C." should read -- 90°C --.
Column 2, line 28 "180°C.," should read -- 180°C, --.
Column 2, line 43 "100°C." should read -- 100°C --.
Column 2, line 57 "250°C." should read -- 250°C --.
Column 2, line 67 "25-35%." should read -- 25-35% by weight --.
Column 3, line 19 "C." should read -- C --.
Column 4, line 9 "250°C." should read -- 250°C --.

Signed and Sealed this
Sixth Day of November, 2012

David J. Kappos
*Director of the United States Patent and Trademark Office*